United States Patent [19]
Rolfe et al.

[11] Patent Number: 5,245,048
[45] Date of Patent: Sep. 14, 1993

[54] PRODUCTION OF GLYCIDYL COMPOUNDS

[75] Inventors: William M. Rolfe, Haverhill; Michael R. Thoseby, Cambridge, both of England

[73] Assignee: Ciba-Geigy Corporation, Ardsley, N.Y.

[21] Appl. No.: 805,430

[22] Filed: Dec. 11, 1991

[30] Foreign Application Priority Data

Dec. 18, 1990 [GB] United Kingdom ............... 9027448

[51] Int. Cl.$^5$ ............... C07D 301/28; C07D 303/04; C07D 303/32
[52] U.S. Cl. ................... 549/516; 549/521
[58] Field of Search ............... 549/516, 521

[56] References Cited

U.S. PATENT DOCUMENTS

| | | | |
|---|---|---|---|
| 2,951,854 | 9/1960 | Chiddix et al. | 549/516 |
| 4,110,354 | 8/1978 | Bertram et al. | 549/516 |
| 4,778,863 | 10/1988 | Wang et al. | 549/516 |

FOREIGN PATENT DOCUMENTS

| | | | |
|---|---|---|---|
| 0110749 | 10/1983 | European Pat. Off. | |
| 658132 | 4/1979 | U.S.S.R. | 549/516 |
| 827450 | 2/1960 | United Kingdom | 549/516 |

OTHER PUBLICATIONS

Houben-Weyl, Methoden Der Organischen Chemie, vol. XIV/2, No. 2, 1963, pp. 475-477.
Houben-Weyl, Methoden Der Organischen Chemie, vol. 20E, 1987; pp. 1911-1924, "Makromolekulare Stoffe" the Journal of Organic Chemistry, vol. 52, No. 6, 1987, pp. 1017-1021.
Tetrahedron, vol. 42, No. 24, 1986, pp. 6573-6614.

*Primary Examiner*—Joseph E. Evans
*Attorney, Agent, or Firm*—William A. Teoli, Jr.

[57] ABSTRACT

A process for the production of a glycidyl ether of an alcohol, comprising reacting an alcohol with epichlorohydrin, in substantially the stoichiometric proportions required to produce the 1:1 adduct, in the presence, as catalyst, of a salt of perchloric acid or trifluoromethane sulphonic acid with a metal of Group IIIA of the Periodic Table of Elements (according to the IUPAC 1970 convention); and then dehydrochlorinating the product so obtained.

14 Claims, No Drawings

PRODUCTION OF GLYCIDYL COMPOUNDS

The present invention relates to a process for the production of glycidyl compounds.

The addition reaction between epoxides and alcohols, in the presence of a catalyst, to produce an ether-alcohol is well known.

In U.S. Pat. No. 4,543,430, there is described a process for the preparation of addition products of epoxides and hydroxylated compounds. The epoxide used is an alkylene oxide or epichlorohydrin and the hydroxylated compound is an alcohol, an alkyleneglycol monoalkylether, a phenol compound or water, the ratio of the hydroxylated compound/epoxide being between 2 and 20 by weight. The reaction is carried out in a homogeneous liquid phase at a temperature between 40° and 250° C. The catalyst is a) a tetra-alkylammonium triflate or b) a trifluoromethanesulphonic acid salt of an alkali metal, a metal of Group II of the Periodic Table of Elements, aluminium, cobalt, nickel, zirconium or tin. The catalyst concentration in the reaction mixture is from 1 to 100 ppm.

The process described in U.S. Pat. No. 4,543,430 has certain deficiences. Although the catalyst used is described as highly active and highly selective, the asserted high selectivity is ensured not so much by the nature of the catalyst, as by the use of a large excess of the hydroxylated compound, relative to the epoxide (see column 2, lines 51 to 53 of U.S. Pat. No. 4,543,430), thereby guaranteeing more of the desired 1:1 epoxide: hydroxylated compound adduct, but resulting in increased process costs.

Surprisingly, we have now found that by choosing, as catalyst, a specific metal salt of perchloric acid or trifluoromethane sulphonic acid (triflic acid) namely a salt of a metal of Group IIIA of the Periodic System, reaction of epichlorohydrin with an alcohol, followed by dehydrochlorination produces a high degree of selectivity for the 1:1 glycidylated alcohol product, while using only substantially stoichiometric amounts of the epichlorhydrin and the alcohol. The amount of included chlorine is significantly reduced compared to chlorine contents of epoxy resins prepared using conventional catalysts.

Accordingly, the present invention provides a process for the production of a glycidyl ether of an alcohol, comprising reacting an alcohol with epichlorohydrin, in substantially the stoichiometric proportions required to produce the 1:1 adduct in the presence, as catalyst, of a salt of perchloric acid or of trifluoromethanesulphonic acid with a metal of Group IIIA of the Periodic Table of Elements (according to the IUPAC 1970 convention); and then dehydrochlorinating the product so obtained.

Preferably, the Group IIIA metal salts are those of lanthanum, cerium, ytterbium or yttrium.

The amount of the Group IIIA perchlorate or triflate catalyst present in the alcohol/epichlorohydrin reaction mixture generally ranges from 0.1 to 10 parts by weight, preferably from 0.1 to 2 parts by weight per 100 parts by weight of the alcohol reactant.

The alcohol reactant may be a primary, secondary or tertiary alcohol. While monohydric alcohols may be used, e.g. a straight- or branched $C_1$-$C_{12}$ primary-, secondary- or tertiary aliphatic monohydric alcohol such as methanol, ethanol, n-propanol, isopropanol, tert-butanol, 2-ethyl-1-hexanol, n-hexanol, n-octanol, n-decanol or n-dodecanol, preferably the alcohol reactant contains two or more hydroxyl groups per molecule.

Preferred polyhydroxy reactants are those having the formula;

$$Q(OH)_m \qquad \qquad I$$

wherein m is an integer from 2 to 10, preferably 2 to 6 and Q is an m-valent aliphatic, cycloaliphatic or araliphatic residue. When Q is a divalent residue, it may be, e.g., a straight chain or branched alkylene residue; or a cycloalkylene residue in which the ring may be optionally substituted, e.g. by alkyl groups or interrupted by heteroatoms, e.g. O or S atoms or several cycloalkyl residues may be bonded together, optionally via a bridge member. When Q is trivalent or a higher valency, Q may be an organic residue having aliphatic, cycloaliphatic or araliphatic structural elements. Q may be substituted with functional groups provided that such groups do not inactivate the Group IIIA metal perchlorate or triflate catalyst and do not undergo competing reactions with epichlorohydrin. Suitable functional groups are, e.g. ester groups as contained in polycaprolactones, and unsaturated groups, e.g. those contained in hydroxyl-terminated polybutadienes or polybutadiene copolymers.

Specific examples of preferred aliphatic diol reactants of formula I include diethylene glycol, triethylene glycol and higher polyoxyethylene glycols; propane-1,2-diol, propane-1,3-diol and higher polyoxypropylene glycols; neopentyl glycol; butane-1,4-diol, and higher poly(oxytetramethylene)glycols; pentane-1,5-diol; hexane-1,6-diol; and octane-1,8-diol;

Examples of preferred aliphatic triols of formula I are 1,1,1-trimethylolpropane, glycerol and 1,1,1-trimethylolethane. Other triols of formula I which are commercially-available and are preferred for use in the present invention include adducts of simple polyols such as glycerol, hexane-1,2,5-triol, hexane-1,2,6-triol, hexane-2,4,6-triol with propylene oxide and/or ethylene oxide.

Tetrafunctional aliphatic alcohols which are preferred include pentaerythritol and 3,3,7,7-tetra(hydroxymethyl)-5-oxanonane.

Preferred higher aliphatic poly-hydroxy compounds include dipentaerythritol, tripentaerythritol, mannitol, sorbitol, polyvinyl alcohol, partially hydrolyzed polyvinyl esters of acetals, and hydroxyalkyl acrylate, methacrylate or itaconate polymers and copolymers.

Preferred cycloaliphatic alcohols of formula I include resorcitol, quinitol, bis(4-hydroxycyclohexyl)methane, 2,2-bis(4-hydroxycyclohexyl)propane, cyclohexanedimethanol and 1,1-bis(hydroxymethyl)cyclohex-3-one.

Alcohols of formula I having araliphatic residues include N,N-bis(2-hydroxyethyl)aniline and $p,p'$-bis(N-(2-hydroxyethyl)aminophenyl)methane.

Alcohols of formula I containing further functional groups which are preferred include polycaprolactone diols and polyols and derivatives of poly(epichlorohydrin).

Other alcohols of interest are adducts of an alkylene oxide, e.g. ethylene oxide or propylene oxide with mononuclear phenols such as resorcinol or hydroquinone, and polynuclear phenols such as bis(4-hydroxyphenyl)methane, bis(4-hydroxyphenyl)sulphone, 1,1,2,2-tetrakis(4-hydroxyphenyl)ethane, 2,2-bis(4-hydroxyphenyl)propane, 2,2-bis(3,5-dibromo-4-hydroxyphenyl)propane, and novolacs formed from aldehydes such as formaldehyde, acetaldehyde, chloral and furfuraldehyde, with phenols such as phenol itself, 4-chlorophenol, 2-methylphenol and 4-tert butylphenol. Further alcohols of interest are styrene-allyl alcohol copolymers.

The process according to the present invention is conveniently conducted by firstly heating a mixture of the alcohol reactant and the Group IIIA perchlorate or triflate catalyst, preferably with agitation, until a liquid solution is obtained. When the temperature of the solution reaches a temperature within the range of from 50° C. to 200° C., especially a temperature within the range of from 100° C. to 150° C., the epichlorhydrin is conveniently added, preferably with agitation of the reaction mixture. Any exothermic reaction which occurs may be controlled and the reaction temperature maintained within the preferred limits, by applying external cooling in conventional manner. The epichlorohydrin is preferably added, portionwise, over an extended period e.g. over a period ranging from 10 minutes up to 10 hours. The alcohol/epichlorohydrin reaction is preferably conducted in the absence of an inert solvent.

When the alcohol/epichlorhydrin reaction is judged to have been completed, the usual time required ranging from 1 to 5 hours, the reaction mixture is cooled, if necessary, to a temperature within the range of from 30° to 100° C. and dehydrochlorination of the reaction product is conducted in conventional manner. Dehydrochlorination may be performed, e.g. by adding to the alcohol/epichlorohydrin addition product an alkali metal hydroxide, in particular sodium hydroxide or potassium hydroxide, optionally together with a quarternary ammonium halide, e.g. tetramethylammonium chloride or benzyltrimethylammonium chloride, as catalyst. If desired, the dehydrochlorination reaction may be performed in the presence of a solvent e.g. 2-methoxyethanol, isodecanol, ethylene glycol, diethylene glycol, N-methylpyrrolidone, gamma-butyrolactone, benzyl alcohol, dibutyl phthalate, methyl ethylketone or toluene. The dehydrochlorinating agent is preferably added portionwise, preferably in solid form, over an extended period, e.g. over a period ranging from 10 minutes to 6 hours.

The dehydrochlorination reaction mixture may be worked up in conventional manner e.g. by washing with water and separating and purifying, e.g. by distillation, the organic phase containing the desired glycidylated alcohol product.

The glycidylated alcohol epoxy resins obtained according to the process of the present invention may be cured in conventional manner or used as diluents for other epoxy resins so cured. Curing agents which may be used include aliphatic amines; dicyandiamide; aromatic amines such as bis(3-aminophenyl)-and bis(4-aminophenyl)sulphone and bis(4-aminophenyl)methane, which are usually used together with an accelerator such as a $BF_3$-amine complex; and carboxylic acids, polycarboxylic acid anhydrides such as phthalic anhydride, cyclohexane-1,2-dicarboxylic acid anydride, methylbicyclo [2,2,1] hept-5-ene-2,3-dicarboxylic acid anhydride, pyromellitic acid dianhydride and benzophenone tetracarboxylic acid dianhydride.

The present invention also provides cured products, e.g. castings or fibre-reinforced composites, comprising a material obtained by curing a glycidylated alcohol epoxy resin produced by a process according to the present invention.

EXAMPLE 1

1,4-butanediol (90 g) is placed in a 3-necked round bottom flask and the catalyst, lanthanum triflate (0.2 g) is added. The mixture is heated with stirring, to the reaction temperature (115°–120° C.), at which point epichlorohydrin (185 g) is added over a one hour period, controlling the exotherm with an ice bath, when necessary.

After heating for sufficient time to enable the reaction to go to completion, the mixture is cooled to 40°–45° C. The reaction product so obtained is dehydrochlorinated with sodium hydroxide (81 g), added in 12 portions over 45 minutes, adding the first aliquot as a 50% aqueous solution. After 30 minutes, 285 ml of water are added, and the organic phase is separated; the solvent is removed at 100° C. under vaccum and the residue is filtered.

The product so obtained has an epoxide value of 8.3 moles $kg^{-1}$ and a total chlorine content of 4.5%.

EXAMPLE 2

The method of Example 1 is repeated except that the catalyst used is cerium (III) triflate (1.0 g).

The product so obtained has an epoxide value of 8.0 moles $kg^{-1}$ and a total chlorine content of 5.6%.

EXAMPLE 3

The method of Example 1 is repeated using as reactants, 2-ethyl-1-hexanol (65.1 g), epichlorohydrin (46.2 g) and lanthanum triflate (0.5 g). Dehydrochlorination using sodium hydroxide (26.6 g) yields a product with an epoxide value of 4.7 mole $kg^{-1}$ and a total chlorine content of 1.9%.

EXAMPLE 4

2,2-bis(4-hydroxycyclohexyl) propane (100 g) is placed in a flange flask, together with lanthanum triflate (0.25 g). The mixture is heated to melting, at which point the epichlorohydrin (75 g) is added over 30 minutes.

After heating to 130° C. for 3 hours, or as long as is necessary for complete reaction, the mixture is cooled to 60° C. and methyl ethyl ketone (200 ml) and tetramethylammonium chloride (50% aqueous) (0.6 g) are added.

The mixture is dehydrochlorinated with sodium hydroxide (31.7 g) at 60°–65° C. The sodium hydroxide is added in 6 portions, over a one hour period, adding the first aliquot as a 50% aqueous solution. After 30 minutes, water (155 ml) is added. The organic phase is separated, solvent is removed at 100° under vacuum and the residue is filtered. The product so obtained has an epoxide value of 4.4 mole $kg^{-1}$ and a total chlorine content of 2.5%.

EXAMPLE 5

The method of Example 4 is repeated in order to glycidylate cyclohexanedimethanol (50 g) using lanthanium triflate (0.2 g), epichlorohydrin (63.8 g) and sodium hydroxide (26.4 g).

The product so obtained has an epoxide value of 6.5 mole $kg^{-1}$ and a total chlorine content of 2.9%.

EXAMPLE 6

The method of Example 4 is repeated in order to glycidylate polypropylene glycol 425 (42.5 g) using lanthanum triflate (0.5 g), epichlorohydrin (18.1 g) and sodium hydroxide (7.6 g). The product so obtained has an epoxide value of 2.7 mole kg$^{-1}$ and a total chlorine content of 2.2%.

EXAMPLE 7

The method of Example 4 is repeated but using 3,3,7,7-tetra(hydroxymethyl)-5-oxanonane (Perstorp Di-TMP) (50 g), lanthanum triflate (0.2 g), epichlorohydrin (72.2 g) and sodium hydroxide (30.5 g).

The product so obtained has an epoxide value of 6.2 mole kg$^{-1}$ and a total chlorine content of 2.8%.

EXAMPLE 8

The method of Example 4 is repeated in order to glycidylate cyclohexanedimethanol (50 g) using ytterbium triflate (1.0 g), epichlorohydrin (63.8 g) and sodium hydroxide (26.4 g).

The product so obtained has an epoxide value of 6.2 mole kg$^{-1}$ and a total chlorine content of 3.9%.

EXAMPLE 9

The method of Example 4 is repeated in order to glycidylate cyclohexanedimethanol (50 g) using yttrium triflate (1.0 g), epichlorohydrin (63.8 g) and sodium hydroxide (26.4 g).

The product so obtained has an epoxide value of 6.2 mole kg$^{-1}$ and a total chlorine content of 4.2%.

EXAMPLE 10

1.4-Butanediol (90 g, 1 mole) is placed into a 3-necked round bottom flask and the catalyst, lanthanum perchlorate (0.25 g,) is added. The mixture is heated, with stirring, to the reaction temperature (100°-105° C.) when the epichlorohydrin (185 g, 2 moles) is added, over a 1 hour period. Any exotherm is controlled with an ice bath.

After heating for sufficient time to allow the reaction to go to completion, the mixture is cooled to 40°-45° C. and dehydrochlorinated with sodium hydroxide (81 g, 2.025 moles), which is added in 12 portions over 45 minutes, adding the first aliquot as a 50% aqueous solution. After 1 hour, 285 ml water are added and the organic phase is separated off, the solvent is removed at 100° C. under vacuum and filtered.

The product has an epoxide value of 8.3 mol/kg and a total chlorine content of 3.6%.

EXAMPLE 11

The method of Example 10 is repeated using cerium perchlorate (0.54 g,) as catalyst.

The product has an epoxide content of 8.2 mol/kg and a total chlorine content of 4.2%.

EXAMPLE 12

The method of Example 10 is repeated in order to glycidylate 2-ethyl-1-hexanol (65.1 g, 0.5 moles) using lanthanum perchlorate (0.5 g), epichlorohydrin (46.2 g, 0.5 moles) and sodium hydroxide (26.6 g, 0.665 moles).

The product so obtained has an epoxide value of 4.9 mol/kg and a total chlorine content of 2.2%.

EXAMPLE 13

Cyclohexanedimethanol (50 g, 0.347 moles) is placed into a 3-necked round bottom flask and the catalyst, ytterbium perchlorate (0.5 g), is added. The mixture is heated, with stirring, to the reaction temperature (130° C.), whereupon the epichlorohydrin (63.8 g, 0.6897 moles) is added over a 1 hour period. Any exotherm is controlled with an ice bath.

After heating for sufficient time to enable the reaction to go to completion, the mixture is cooled to 60° C. and methyl ethyl ketone (200 ml) and tetramethylammonium chloride (50% aqueous) (0.6 g) are added.

The mixture is dehydrochlorinated with sodium hydroxide (26.4 g, 0.66 moles), added in 8 portions over 1 hour. After 1 hour, 155 ml water are added. The organic phase is separated off, the solvent removed at 100° C. under vacuum and filtered. The product has an epoxide value of 6.5 mol/kg and a total chlorine content of 3.1%.

EXAMPLE 14

The method of Example 13 is repeated using yttrium perchlorate (0.5 g) as catalyst. The product so obtained has an epoxide value of 6.5 mol/kg and a total chlorine content of 3.0%.

EXAMPLE 15

The method of Example 13 is repeated in order to glycidylate 2,2-bis(4-hydroxycyclohexyl)propane (100 g, 0.42 moles) using lanthanum perchlorate (0.25 g), epichlorohydrin (75.0 g, 0.81 moles) and sodium hydroxide (31.7 g, 0.79 moles).

The product so obtained has an epoxide value of 4.4 mol/kg and a total chlorine content of 3.0%.

EXAMPLE 16

The method of Example 13 is repeated in order to glycidylate polypropylene glycol 425 (42.5 g, 0.1 mol) using lanthanum perchlorate (0.5 g), epichlorohydrin (18.1 g, 0.196 moles) and sodium hydroxide (7.6 g, 0.19 moles).

The product so obtained has an epoxide value of 2.7 mol/kg and a total chlorine content of 2.0%.

EXAMPLE 17

The method of Example 13 is repeated in order to glycidylate 3,3,7,7-tetra(hydroxymethyl)-5-oxanonane (Perstorp Di-Tmp) (50.0 g, 0.20 moles) using lanthanum perchlorate (0.2 g) epichlorohydrin (72.2 g, 0.78 moles) and sodium hydroxide (30.5 g, 0.76 mol).

The product so obtained has an epoxide value of 6.5 mol/kg and a total chlorine content of 4.0%.

We claim:

1. A process for the production of a glycidyl ether of an alcohol, comprising reacting an alcohol with epichlorohydrin, in substantially the stoichiometric proportions required to produce the 1:1 adduct, in the presence, as catalyst, of a salt of perchloric acid or trifluoromethane sulphonic acid with a metal of Group IIIA of the Periodic Table of Elements (according to the IUPAC 1970 convention); and then dehydrochlorinating the product so obtained.

2. A process according to claim 1 in which the catalyst is a salt of perchloric acid with a metal of Group IIIA.

3. A process according to claim 1 in which the catalyst is a salt of trifluoromethane sulphonic acid with a metal of Group IIIA.

4. A process according to claim 1 in which the Group IIIA metal salt is that of lanthanum, cerium, ytterbium or yttrium.

5. A process according to claim 1 in which the amount of the Group IIIA metal salt catalyst present in the alcohol/epichlorohydrin reaction mixture ranges from 0.1 to 10 parts by weight based on 100 parts by weight of the alcohol reactant.

6. A process according to claim 5 in which the amount of the Group IIIA metal salt catalyst present in the alcohol/epichlorohydrin reaction mixtures ranges from 0.1 to 2 parts by weight, based on 100 parts by weight of the alcohol reactant.

7. A process according to claim 1 in which the alcohol reactant is a straight- or branched chain $C_1$–$C_{12}$ primary, secondary, or tertiary aliphatic monohydric alcohol.

8. A process according to claim 7 in which the aliphatic alcohol is methanol, ethanol, n-propanol, isopropanol, tert-butanol, 2-ethyl hexanol, n-hexanol, n-octanol, n-decanol or n-dodecanol.

9. A process according to claim 1 in which the alcohol reactant is a compound of formula I:

$$Q(OH)_m \qquad \qquad I$$

wherein m is an integer from 2 to 10 and Q is an m-valent aliphatic, cycloaliphatic or araliphatic residue.

10. A process according to claim 9 in which m is an integer from 2 to 6.

11. A process according to claim 9 in which the alcohol reactant is an aliphatic diol and is diethylene glycol, triethylene glycol or a higher polyoxyethylene glycol; propane-1,2-diol, propane-1,3-diol or a higher polyoxypropylene glycol; neopentyl glycol; butane-1,4-diol or a higher poly(oxytetramethylene) glycol pentane-1,5-diol; hexane-1,6-diol; or octane-1,8-diol; the alcohol reactant is an aliphatic triol and is 1,1,1-trimethylolpropane, glycerol, 1,1,1-trimethylolethane, or an adduct of glycerol, hexane-1,2,5-triol, hexane-1,2,6-triol or hexane-2,4,6-triol with propylene oxide and/or ethylene oxide; the alcohol reactant is an aliphatic tetrol and is pentaerythritol or 3,3,7,7-tetra(hydroxymethyl)-5-oxanonane; the alcohol reactant is dipentaerythritol, mannitol, sorbitol, polyvinyl alcohol, partially hydrolyzed polyvinyl esters or acetals and hydroxyalkyl acrylate, methacrylate or itaconate polymers or copolymers, or poly(epichlorohydrin)s; the alcohol reactant is a cycloaliphatic alcohol and is resorcitol, quinitol, bis(4-hydroxycyclohexyl)methane, 2,2-bis(4-hydroxycyclohexyl)propane, cyclohexane dimethanol or 1,1-bis(-hydroxymethyl)cyclohex-3-ene; the alcohol reactant has an araliphatic residue and is N,N-bis(2-hydroxyethyl)aniline or p,p-bis(N-(2-hydroxyethyl)aminophenyl)methane; the alcohol reactant contains further functional groups and is a polycaprolactone diol or polyol, or a derivative of poly(epichlorohydrin); the alcohol reactant is adduct of an alkylene oxide with a phenol or a novolac formed from an aldehyde and a phenol; the alcohol reactant is an adduct of an alkylene oxide with resorcinol, hydroquinone, bis(4-hydroxyphenyl)methane, bis(4-hydroxyphenyl)sulphone, 1,1,2,2-tetrakis(4-hydroxyphenyl)ethane, 2,2-bis(4-hydroxyphenyl)propane or 2,2-bis(3,5-dilromo-4-hydroxy-phenyl)propane; or the alcohol reactant is a styrene-alkyl alcohol copolymer.

12. A process according to claim 1 in which the alcohol/epichlorhydrin reaction is performed at a temperature within the range of from 50° C. to 200° C. in the absence of an inert solvent.

13. A process according to claim 1 in which the molar ratio of epichlorohydrin to hydroxyl ranges from about 0.97 to 1.1.

14. A process according to claim 1 in which the dehydrochlorination is performed at a temperature within the range of from 30° C. to 100° C.

* * * * *